United States Patent [19]

Baba

[11] 4,374,525

[45] Feb. 22, 1983

[54] ULTRASONIC DIAGNOSTIC APPARATUS FOR ENDOSCOPE

[75] Inventor: Kazuo Baba, Hachioji, Japan

[73] Assignee: Olympus Optical Co., Ltd., Tokyo, Japan

[21] Appl. No.: 258,004

[22] Filed: Apr. 27, 1981

[30] Foreign Application Priority Data

Apr. 28, 1980 [JP] Japan .................. 55-56868

[51] Int. Cl.$^3$ .............................................. A61B 10/00
[52] U.S. Cl. ........................................ 128/660; 128/4; 73/633
[58] Field of Search ................. 73/623, 633, 634, 638, 73/640; 128/4-9, 24 A, 303.15, 660, 661, 662, 663; 356/241

[56] References Cited

U.S. PATENT DOCUMENTS

| | | | |
|---|---|---|---|
| 3,779,234 | 12/1973 | Eggleton et al. | 128/24 A |
| 3,817,089 | 6/1974 | Eggleton et al. | 128/661 |
| 3,942,530 | 3/1976 | Northeved | 128/303.15 |
| 3,955,561 | 5/1976 | Eggleton | 128/660 |
| 4,008,603 | 2/1977 | Paulissen . | |
| 4,327,738 | 5/1982 | Green et al. | 128/660 |

FOREIGN PATENT DOCUMENTS

| | | | |
|---|---|---|---|
| 2950203 | 6/1980 | Fed. Rep. of Germany | 128/660 |
| 30-5414609 | 3/1955 | Japan . | |
| 49-1670 | 1/1974 | Japan . | |
| 56-28825 | 5/1981 | Japan | 128/660 |

OTHER PUBLICATIONS

K. Hisanaga et al., Proceedings of the 23rd Annual Meeting of the AINM, 1978.
W. B. Taylor et al., Ultrasound in Medicine and Biology, vol. 5, pp. 129–138, Mar. 9, 1979.

*Primary Examiner*—Richard J. Apley
*Assistant Examiner*—George Yanulis
*Attorney, Agent, or Firm*—Frishauf, Holtz, Goodman and Woodward

[57] ABSTRACT

An insert section of an ultrasonic probe device which is bendably coupled by means of a hinge with two rotation shafts rotatably disposed within an insert section that is coupled to a universal joint. The distal tube can be bent freely by operating a control knob at a control section, so that an ultrasonic transducer member at the tip of the distal tube may be brought closely into contact with the body wall.

7 Claims, 7 Drawing Figures

ULTRASONIC DIAGNOSTIC APPARATUS FOR ENDOSCOPE

BACKGROUND OF THE INVENTION

This invention relates to an ultrasonic diagnostic apparatus, and more specifically to an ultrasonic diagnostic apparatus for an endoscope.

Ultrasonic diagnostic apparatus for an endoscope are classified into two types; one for rigid endoscopes and the other for flexible endoscopes. The ultrasonic diagnostic apparatus for rigid endoscopes have an advantage in being able to provide more accurate positional (angular) information for scanning. As for the ultrasonic diagnostic apparatus for flexible endoscopes, they can vary slicing directions and provide closer contact with the surface of a subject. With the prior art ultrasonic apparatus for rigid endoscopes, however, it is hard to bring the distal insert section of a probe device closely into contact with the surface of the subject. Therefore, the probe device is ultrasonically brought into contact with the subject surface by using a balloon filled with a liquid or by filling the body cavity with the liquid. With these apparatus, moreover, the slicing direction cannot be widely changed, so that the range of diagnosis will be limited in some measure. With the ultrasonic diagnostic apparatus for flexible endoscopes, on the other hand, the scanning position (angle) cannot be accurately detected because of the flexibility of the scanning system although the slicing direction can be varied over a wide range.

It is therefore an object of this invention to provide an ultrasonic diagnostic apparatus for endscopes capable of closely touching the cavity wall of a patient body and setting the slicing direction over a wide range.

SUMMARY OF THE INVENTION

According to this invention, there is provided an ultrasonic diagnostic apparatus for an endoscope which comprises an insert section including at least two rigid tubes connected with each other by means of at least one hinge, at least two rotation shafts disposed severally in the rigid tubes and coupled with each other by means of the universal joint, and at least one ultrasonic transducer fixed to the tip of one of the rotation shafts at the distal end of the insert section; and a control section including a power source disposed at the proximal end of the insert section for rotating the rotation shaft and a driver for driving the rigid distal tube of the insert section to bend.

This invention can be more fully understood from the following detailed description when taken in conjunction with the accompanying drawings.

BRIEF DESCRIPTION OF THE DRAWIGS

DETAILED DESCRIPTION

Figure 1:
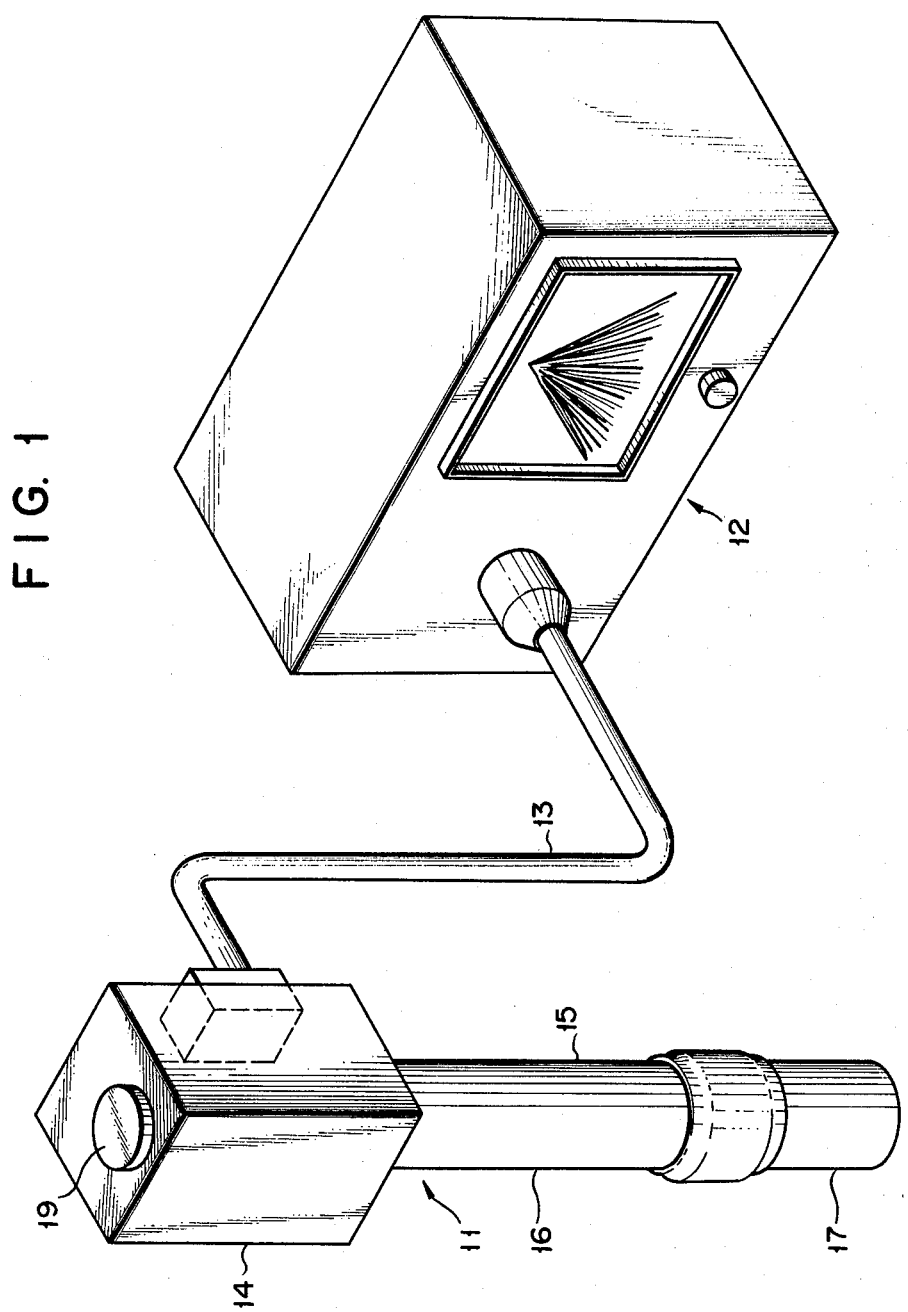
FIG. 1 is a perspective view of an ultrasonic diagnostic apparatus for an endoscope according to an embodiment of this invention.

Referring now to the drawing of FIG. 1, there is shown an ultrasonic diagnostic apparatus which comprises a probe device 11 and an observation device 12 connected with each other by means of a cord 13. The probe device 11 includes a control section 14 and an insert section 15 extending therefrom. The insert section 15 is formed of two rigid tubes 16 and 17 and a hinge 18 bendably connecting these tubes 16 and 17 and enclosed by an elastic tube 15a. The rigid distal tube 17 can be bent at the hinge 18 by operating a control knob 19 at the control section 14.

Figure 2:
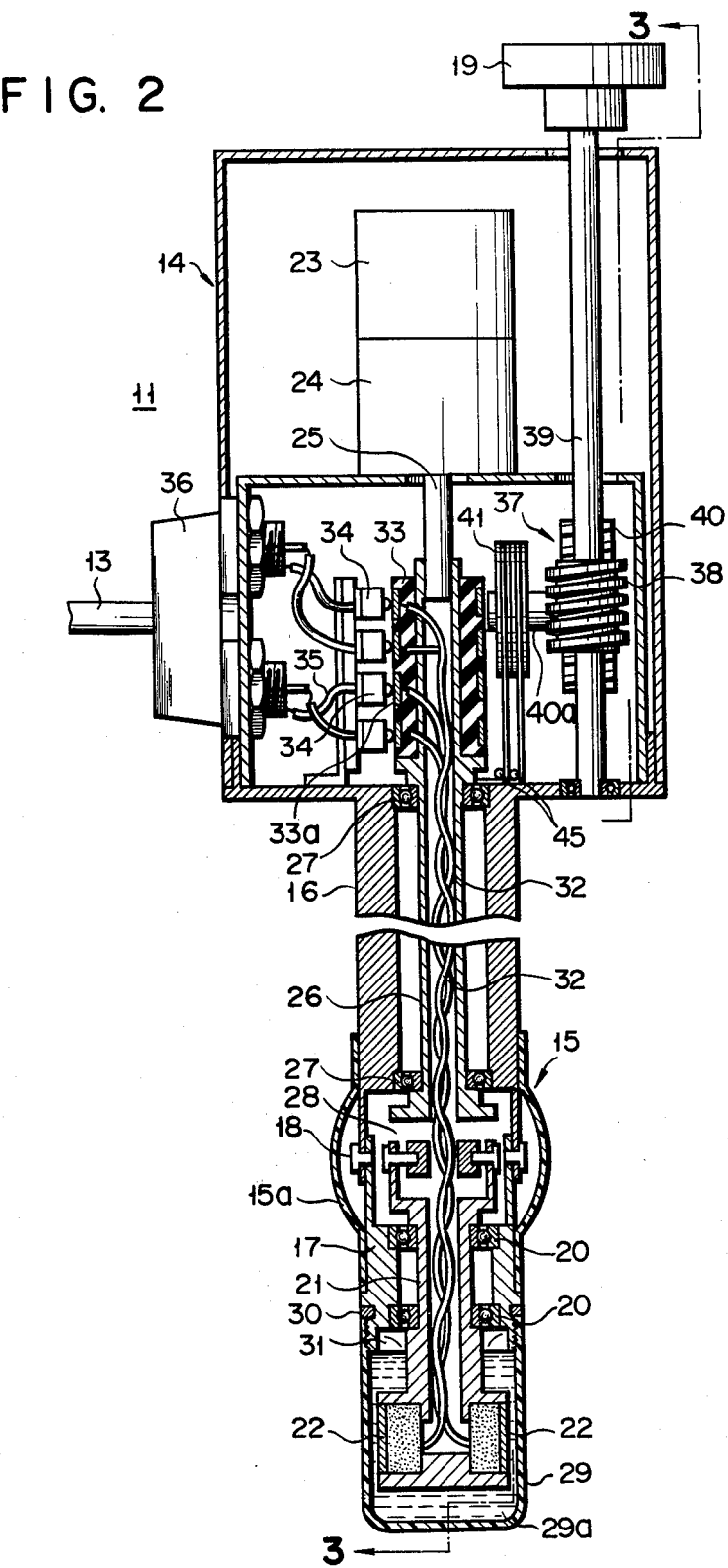
FIG. 2 is a sectional view of a probe device shown in FIG. 1.
Figure 3:
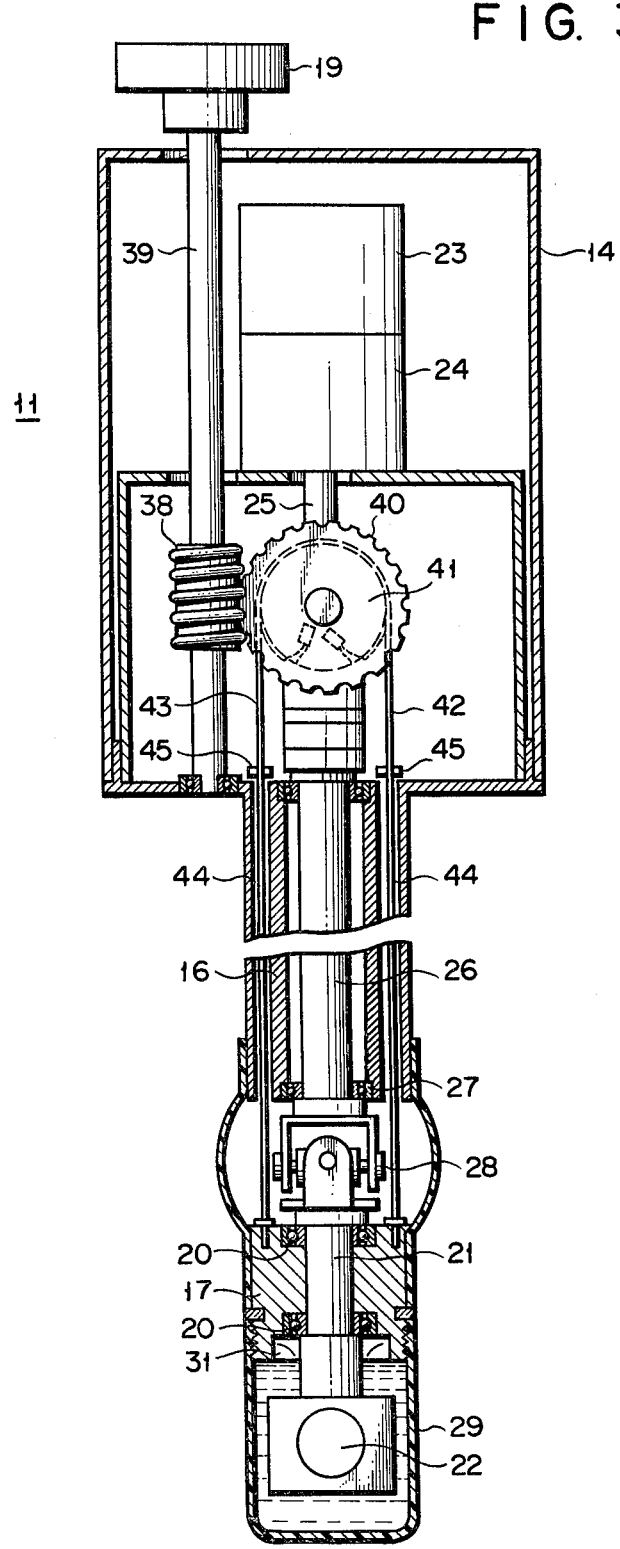
FIG. 3 is a sectional view as taken along line 3—3 of FIG. 2.

In FIGS. 2 and 3 showing the construction of the probe device 11, a cylindrical rotation shaft 21 rotatably supported by bearings 20 is coaxially fitted in the rigid distal tube 17. A plurality of, e.g. two ultrasonic transducers (e.g., piezoelectric elements) 22 are attached to the distal end of the shaft 21. The control section 14 is provided with a motor (e.g., servomotor, stepping motor or synchronous motor) 23 and a rotation angle detector 24 for detecting the rotation angle of the motor 23. The rotation angle detector 24 is formed of a potentiometer whose shaft is coupled to the shaft 25 of the motor 23 to rotate therewith. The shaft 25 of the motor 23 is connected with the proximal end of a rotation shaft 26 which is coaxially fitted in the rigid base tube 16. The rotation shaft 26 is rotatably retained in the rigid base tube 26 by means of bearings 27. The distal end of the shaft 26 is connected with the proximal end of the shaft 21 in the rigid distal tube 17 by means of a universal joint 28.

The ultrasonic transducers 22 are projected from the distal end of the rigid distal tube 17, and is attached to the distal end of the rotation shaft 21 so as to emit ultrasonic beams at right angles to the rotation shaft 21. The ultrasonic transducers 22 are surrounded by a cap 29 which is liquid-tightly, removably attached to the distal end of the rigid distal tube 17. The cap 29 is filled with an ultrasonic permeable medium 29a (e.g., degassed water, physiological salt solution, liquid paraffin, glycerine, etc.). The cap 29 is formed of a material (e.g., plastic) which may cause less reflection and attenuation in the propagation of the ultrasonic beams. An O-ring 30 is interposed between the cap 29 and the rigid distal tube 17, and an oil seal 31 is used at the rotation area between the rigid distal tube 17 and the shaft 21, thereby ensuring the watertightness of the probe device 11.

The ultrasonic transducers 22 are severally connected with respective one ends of coaxial cables 32. The coaxial cables 32 extend into the control section 14 through the interior of the cylindrical shaft 21, the central portion of the universal joint 28, and the interior of the cylindrical shaft 26. Inside the control section 14, the other ends of the coaxial cables 32 are connected with slip rings 33a of a rotating contact member 33 which is fitted on the proximal end portion of the rotation shaft 26. The slip rings 33a are severally in touch with contact brushes 34 which are connected with a connector 36 by means of coaxial cables 35. The connector 36 is removably connected with the observation device 12 by means of the cord 13.

Disposed in the control section 14 is a distal drive assembly 37 which includes a worm gear shaft 39 fitted with a worm gear 38 and rotated by means of the control knob 19, a wheel gear 40 in mesh with the worm gear 38, and a pulley 41 mounted on the shaft 40a of the wheel gear 40. Wires 42 and 43 are oppositely wound around the pulley 41. Respectively each end of the wires 42 and 43 are fixed to the pulley 41, and the other ends are coupled to the proximal end of the distal tube 17 through slots 44 in the tube 16 and the interior of the hinge 18. The wires 42 and 43 are guided into the slots 44 by e.g. rollers 45 so as to be located in the central portion of the insert section 15. The distal ends of the wires 42 and 43 are fixed respectively in positions facing each other with the universal joint 28 between them. Thus, when opposite forces are applied to the wires 42 and 43, the distal tube 17 is bent and moved relatively to the base tube 16 by means of the hinge 18 and the universal joint 28.

Figure 4:
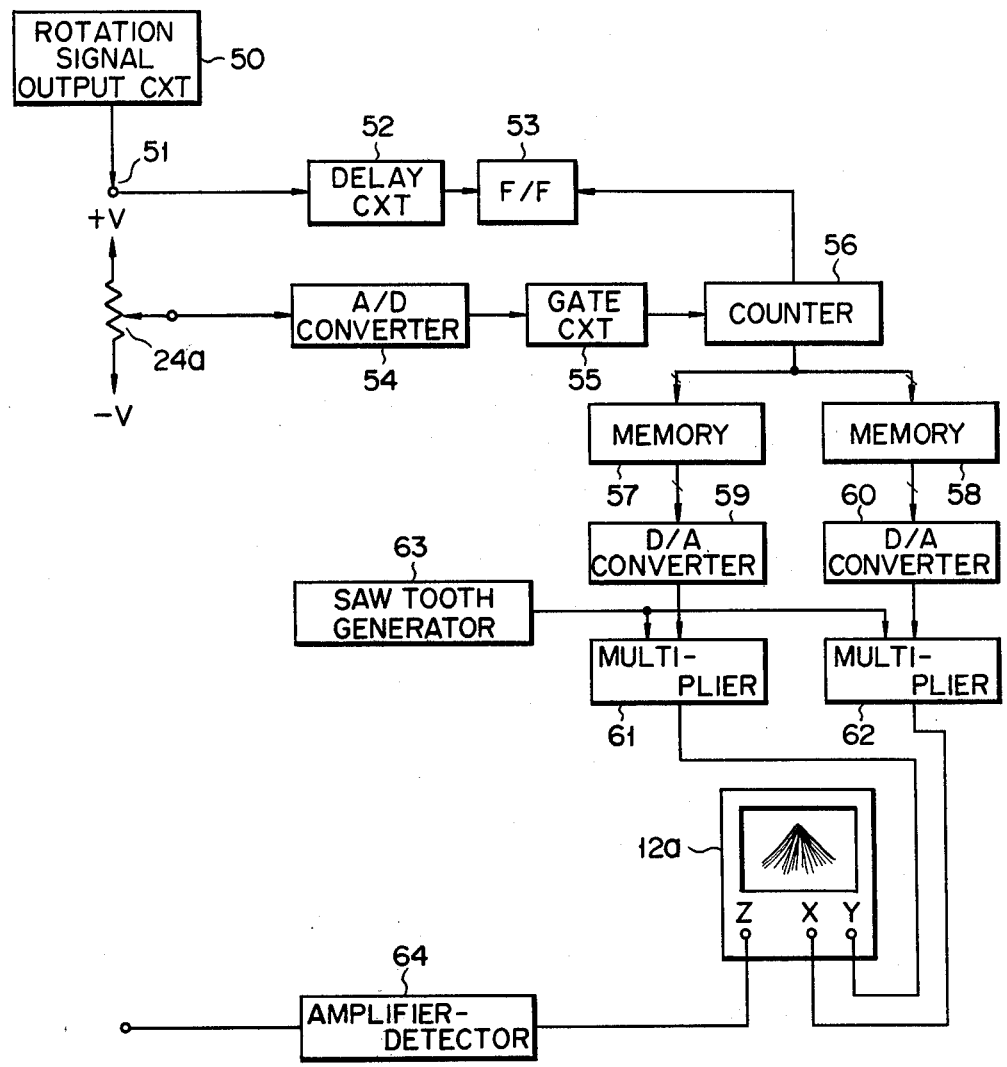
FIG. 4 is a block circuit diagram of the ultrasonic diagnostic apparatus for endoscope of FIG. 1.

Referring now to FIG. 4, there will be described the electric circuit system of the ultrasonic diagnostic apparatus. A terminal 51 connected with a rotation signal output circuit 50 is connected to the set input end of a flip-flop circuit 53 through a delay circuit 52. The rotation signal output circuit 50, which is so designed as to produce an output signal for each revolution of the motor shaft 25, can be formed of a rotation detector circuit which is disposed inside the rotation angle detector 24 and detects the rotation of the motor shaft 25 by e.g. photoelectric conversion. A potentiometer 24a of the rotation angle detector 24 is connected between power sources +V and −V. The output end of the potentiometer 24a, along with the output end of the flip-flop circuit 53, is connected to a gate circuit 55 through an A/D converter 54. The output end of the gate circuit 55 is connected to a counter 56. The counter 56 counts the rotation angle of the motor shaft on the basis of an output signal which is delivered from the potentiometer 24a in accordance with the rotation angle of the motor shaft 25. The output end of the counter 56 is connected to the address designation input ends of memories 57 and 58. These memories 57 and 58 store data corresponding to the value of a function of sine and cosine values for the angle of deflection of an ultrasonic beam. The output ends of the memories 57 and 58 are connected to the input ends of multipliers 61 and 62 through D/A converters 59 and 60, respectively. These multipliers 61 and 62 are further connected with the output end of a sawtooth signal generator 63. The output ends of the multipliers 61 and 62 are connected to the Y- and X-axis signal terminals of a display device 12a, respectively. The Z-axis signal terminal of the display device 12a is connected with the output ends of the transducers 22 through an amplifier-detector circuit 64.

Figure 5:
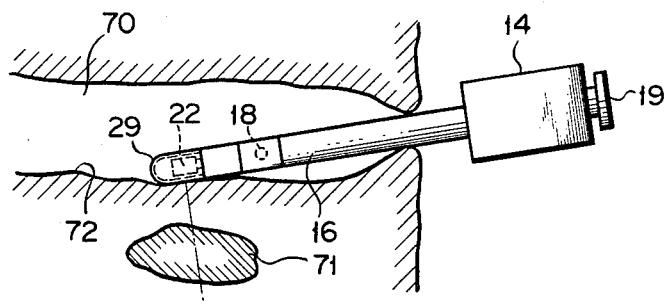
FIGS. 5 to 7 show various states of diagnosis using the probe device.

Now there will be described the operation of the ultrasonic diagnostic apparatus of the above-mentioned construction. First, the insert section 15 of the probe device 11 is inserted into a body cavity 70, and the cap 29 containing the ultrasonic transducers 22 is brought closely into contact with a body wall 72 embracing a subject or affected part 71, as shown in FIG. 5. In this state, when the motor 23, which is supplied with electric power from a power source at the observation device 12 by means of the cord 13, is rotated, and the ultrasonic transducers 22 are driven by driving pulses (e.g., 1 to 10 MHz) from a driving pulse generator at the observation device 12, then the ultrasonic transducers 22 emit an ultrasonic beam while rotating at a speed of e.g. 5 to 900 rpm. Then, the affected part is scanned with the emitted ultrasonic beam. An echo of the ultrasonic beam is received by the ultrasonic transducers 22, and converted into an echo signal. This echo signal is led to the slip rings 33a by the coaxial cables 32, and supplied to the observation device 12 through the contact brushes 34, coaxial cable 35, and connector 36. In the observation device 12, the echo signal is applied to the Z-axis input end of the display device 12a via the amplifier-detector 64. Meanwhile, the output signal of the signal output circuit 50 sets the flip-flop circuit 53 with the aid of the delay circuit 52. The set signal of the flip-flop circuit 53 opens the gate circuit 55, and rotation angle information from the potentiometer 24a, which is converted into a digital signal by the A/D converter 54, is led into the counter 56. The counter 56 counts digital signals each produced every time the slider of the potentiometer 24a moves through a fixed angle. In other words, the counter 56 counts the rotation angle of the motor shaft 25. Addresses for the memories 57 and 58 are designated in accordance with the count number in the counter 56. Digital values for sin $\theta$ and cos $\theta$ information corresponding to the rotation angle or deflection angle $\theta$ of the ultrasonic beam, which have previously been stored in the memories 57 and 58, are successively read out in accordance with the count number in the counter 56. These sin $\theta$ and cos $\theta$ informations are converted into analog signals by the D/A converters 59 and 60 respectively, and supplied to the multipliers 61 and 62 respectively. In the multipliers 61 and 62, the sin $\theta$ analog signal and cos $\theta$ analog signal are multiplied by a sawtooth signal from the sawtooth generator 63. Output signals from the multipliers 61 and 62 are applied to the Y- and X-axis input ends of the display device 12a, respectively. The deflection circuit of the display device 12 is controlled by the output signals of the multipliers 61 and 62, and a slice image corresponding to the echo signal is indicated on the display device 12a. The counter 56 is so designed as to be able to set freely the deflection angle of the ultrasonic beam. If the deflection angle is set to 90°, for example, the counter 56 supplies a reset signal to the flip-flop circuit 53 to reset the same when the deflection angle becomes 90° with respect to the rotation signal generation point where the deflection angle is 0°. As a result, the counter 56 ceases to count when the deflection angle 90° is obtained, so that a sector scan image corresponding to the deflection angle 90° is indicated on the display device 12a. Thus, a selected-angle slice image can be provided for the observation device 12 by freely selecting the set value of deflection angle of the counter 56.

Figure 6:
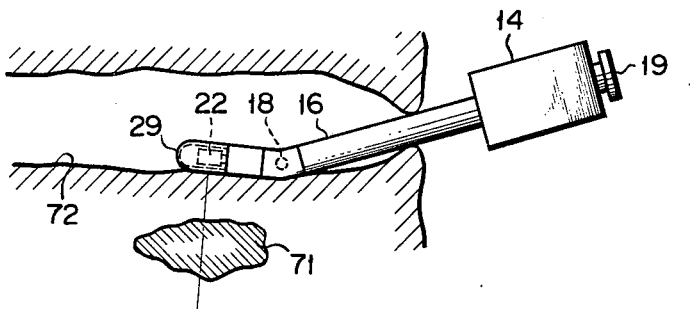
Figure 7:
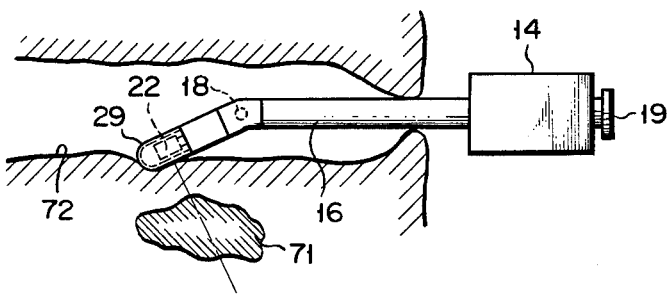

There has been described the way of detecting a slice image in a state where the distal tube 17 is not bent relatively to the base tube 16, as shown in FIG. 5. Referring now to FIG. 6, there will be described a case where a slice image is obtained with use of varied slicing directions. In this case, the control knob 19 is operated so that the distal tube 17 is bent relatively to the base tube 16, as shown in FIG. 6. Thus, the control knob 19 is rotated, so that the worm gear 38 is rotated together with the worm gear shaft 39. Then, the wheel gear 40 and hence the pulley 41 are rotated. The rotation of the pulley 41 causes one of the wires 42 and 43 to be wound up and the other to be loosened. In FIG. 3, for example, when the pulley 41 is rotated in the clockwise direction, the wires 43 and 42 are wound up and loosened, respectively. As a result, the distal tube 17 is bent at the hinge 18 toward the wire 43. When the distal tube 17 is thus bent in accordance with the configuration of the body wall 72, the surface of the ultrasonic transducer section or the side face of the cap 29 is brought in contact with the body wall 72, and a satisfactory slice image of the affected part or organ 71 around the cap 29 is obtained. FIG. 7 shows a state obtained when the control knob 19 is operated in the opposite way to the case of FIG. 6. Thus, the slicing direction can be set freely in accordance with the operation of the control knob 19, permitting a greatly extended range of variation.

According to this invention, as described above, the ultrasonic probe device 11 is so constructed that the distal end portion of the insert section 15 may be bent freely. Despite the rigidity of the insert section 15, therefore, the surface of the ultrasonic transducer section can be easily brought in contact with the surface portion of the body wall embracing the affected part. Thus, the operability is improved, and the range of variation of the slicing direction is widened. Further, the use of a plurality of ultrasonic transducers enables slice image detection at short intervals of time, so that real-time slice images can be obtained.

Although the insert section is formed of two rigid tubes, base and distal, in the aforementioned embodiment, the probe device may alternatively include three or more tubes bendably coupled by means of hinges. Moreover, the ultrasonic beam and ultrasonic echo may be transmitted and received through a rotation mirror without rotating the ultrasonic transducer.

What is claimed is:

1. An ultrasonic diagnostic apparatus comprising: an insert section including at least a rigid base tube and a rigid distal tube bendably coupled with each other by at least one hinge means, first and second rotation shafts rotatably disposed in said rigid base and distal tubes respectively and coupled with each other by at least one universal joint, and ultrasonic transducer means including an ultrasonic scanning member disposed at the distal end of said rigid distal tube and attached to the distal end of said second rotation shaft; and
  a control section including a rotation driving source for supplying rotation driving force to said first and second rotation shafts and a bending drive means for driving said distal tube to bend.

2. An ultrasonic diagnostic apparatus according to claim 1, wherein said ultrasonic transducer means comprises at least one ultrasonic transducer attached to said ultrasonic scanning member and rotated together with said first and second rotation shafts, a cap surrounding said ultrasonic transducer, and an ultrasonic permeable medium filling said cap.

3. An ultrasonic diagnostic apparatus according to claim 1 or 2, wherein said bending drive means comprises a control knob disposed on said control section and a driving force transmitting means for converting a driving force applied to said control section into a bending force and transmitting said bending force to said rigid distal tube.

4. An ultrasonic diagnostic apparatus according to claim 1, wherein said control section includes a rotation angle detector for detecting the rotation angle of said rotation driving source, whereby the ultrasonic scanning angle is determined on the basis of the detection output of said rotation angle detector.

5. An ultrasonic diagnostic apparatus according to claim 1 or 2, wherein said ultrasonic transducer means inclusdes a plurality of ultrasonic transducers.

6. An ultrasonic diagnostic apparatus comprising:
  an ultrasonic probe device constituted by an insert section including at least a rigid base tube and a rigid distal tube bendably coupled with each other by at least one hinge means, first and second rotation shafts rotatably disposed in said rigid base and distal tubes respectively and coupled with each other by at least one universal joint, and ultrasonic transducer means including a plurality of ultrasonic transducers disposed at the distal end of said rigid distal tube and attached to the distal end of said second rotation shaft; and a control section including a rotation driving source for supplying rotation driving force to said first and second rotation shafts to rotate said ultrasonic transducers, a bending drive means for driving said rigid distal tube to bend, and a rotation angle detector for detecting the rotation angle of said rotation driving source; and
  an observation device including a signal transmitter-receiver means connected to said ultrasonic probe device, whereby driving pulses are supplied to said ultrasonic transducer means and echo signals are received, and a display means for indicating a slice image corresponding to the echo signals from said signal transmitter-receiver means.

7. An ultrasonic diagnostic apparatus according to claim 6, wherein said ultrasonic transducer means comprises a cap surrounding said ultrasonic transducers and an ultrasonic permeable medium filling said cap.

* * * * *